(12) United States Patent
Hignight et al.

(10) Patent No.: US 7,368,638 B2
(45) Date of Patent: May 6, 2008

(54) TETRAPLOID PERENNIAL RYEGRASS VARIETY T3

(76) Inventors: Kenneth Hignight, 613 S. 3rd, Jefferson, OR (US) 97352; Debra Rush, 3483 Madison, Albany, OR (US) 97322

(*) Notice: Subject to any disclaimer, the term of this patent is extended or adjusted under 35 U.S.C. 154(b) by 0 days.

(21) Appl. No.: 11/281,287

(22) Filed: Nov. 17, 2005

(65) Prior Publication Data

US 2006/0143741 A1 Jun. 29, 2006

Related U.S. Application Data

(60) Provisional application No. 60/638,894, filed on Dec. 23, 2004.

(51) Int. Cl.
*A01H 5/00* (2006.01)
*A01H 5/10* (2006.01)
*A01H 1/00* (2006.01)

(52) U.S. Cl. .................. 800/320; 800/298; 800/260

(58) Field of Classification Search ................ 800/260, 800/276, 298, 320, 323
See application file for complete search history.

(56) References Cited

OTHER PUBLICATIONS

Fehr. 1987. Principles of cultivar development, vol. 1, Theory and Technique, p. 519.*
Bonos et al. 2004. Crop Sci. 44: 350-351.*
Smith et al. 2001. J. Agric. Sci. 136: 65-74.*
Harivandi. 1986. California Turfgrass Culture, vol. 36, Nos. 1-4, pp. 1-4.*
Ahloowalia. 1967. Genetica 38: 471-484.*
Jensen, K.B., Wldron, B.L., Asay, K.H., Johnson, D.A., Monaco, T.A., Forage Nutritional Characteristics of Orchardgrass and Perennial Rygrass at Five Irrigation Levels, Agronomy Journal, 2003, 668-675, 95, United States.
Jensen, K.B., Asay, K.H., Waldron, B.L., Dry Matter Production of Orchardgrass and Perennial Ryegrass at Five Irrigation Levels, Crop Science, 2001, 479-487, 41, United States.
Sanderson, M.A., Elwinger, G.F., Emergence and Seedling Structure of Temperate Grasses at Different Planting Depths, Agronomy Journal, 2004, 685-691, 96, Wisconsin.
Sugiyama, S., Polyploidy and Cellular Mechanisms Changing Leaf Size: Comparison of Diploid and Autotetraploid Populations in Two Species of Loium, Annals of Botany, 2005, 931-938, 96, Oxford University Press.
Warnock, D.L., Leep, R.H., Bughrara, S.S., Min, D.-H., Cold Tolerance Evaluation of Improved Diploid and Tetraploid Cultivars of Perennial Ryegrass.
Sugiyama, S., Differentiation in Competitive Ability and Cold Tolerance Between Diploid and Tetraploid Cultivars in Lolium Perenne, Euphytica, 1998, 55-59, 103, Kluwer Academic Publishers, Netherlands.
Norrington-Davies, J., Harries, J.H., Competition studies in diploid and tetraploid varieties of Lolium perenne, 1977, 405-410, 88, Great Britain.
Frame, J., Merrilees, D.W., The effect of tractor wheel passes on herbage production from diploid and tetraploid ryegrass swards, Grass and Forage Science, 1996, 13-20, 51, Scotland, UK.
Smith, K.F., Simpson R.J., Culvenor, R.A., Humphreys, M.O., Prud-Homme, M.P., Oram, R.N., The effects of ploidy and a phenotype conferring a high water-soluble carbohydrate concentration on carbohydrate accumulation, nutritive value and morphology of perennial ryegrass (Lolium perenne L.), Journal of Agricultural Science, 2001, 65-74, 136, Cambidge University Press, Cambidge, UK.

* cited by examiner

*Primary Examiner*—David H. Kruse
*Assistant Examiner*—Keith O. Robinson

(57) ABSTRACT

A tetraploid perennial ryegrass variety known as breeder's code T3, and seed used to produce the grass are provided. The grass is useful as a short lived, improved turfgrass on golf courses, athletic fields and other areas using seeded turfgrasses. The grass is also useful in overseeding of dormant warm season grasses since its lack of heat tolerance allows for a smooth transition for the warm-season grass. The ryegrass will provide a green cover during the winter months but will die out when the temperatures increases to the point which allow the warm-season grass to grow.

9 Claims, No Drawings

TETRAPLOID PERENNIAL RYEGRASS VARIETY T3

This application claims priority to U.S. patent application Ser. No. 60/638,894, filed Dec. 23, 2004.

BACKGROUND OF THE INVENTION

1. Field of the Invention

This invention relates to cultivated varieties of true breeding, stable, tetraploid perennial ryegrass, for use as a short lived, improved turfgrass on golf courses, athletic fields and other areas using seeded turfgrasses.

2. Background of the Art

Tetraploid perennial ryegrass is commonly used as a forage grass. It is not used, nor recommended, for turfgrass use. Typical tetraploid ryegrass produces an open sward and has a very rapid vertical extension rate. Commercial varieties are light green in color. There are no commercially available varieties of tetraploid perennial ryegrass available for permanent or overseeding turf use.

A stable variety of tetraploid perennial ryegrass would be a desirable grass for use in overseeding of dormant warm season grasses since its lack of heat tolerance allows for a smooth transition for the warm-season grass. Tetraploid perennial ryegrass will provide a green cover during the winter months but will die out when the temperatures increase which allow the warm-season grass to grow.

For many southern golf courses planted with Bermuda grass, a standard practice is to overseed every fall with diploid perennial ryegrass. Diploid perennial ryegrass provides an outstanding turf cover during the cool winter months. However, diploid perennial ryegrass is very persistent and does not easily die out and give way for the re-emerging Bermuda grass in the spring when warm weather returns.

Turfgrass managers could utilize a cultivar that has a dark green color, rapid establishment, and the ability to transition rapidly. The two most widely used species for overseeding are annual and diploid perennial ryegrass. Annual ryegrass, such as the variety 'Gulf,' have an undesirable color and a very rapid vertical extension rate which results in frequent mowing. Diploid perennial ryegrass has been developed for heat tolerance and permanent turf use and therefore does not transition well.

SUMMARY OF THE INVENTION

A tetraploid perennial ryegrass variety known as breeder's code T3, and methods used to produce the grass are provided. The grass is useful as a short lived, improved turfgrass on golf courses, athletic fields and other areas using seeded turfgrasses. The grass is also useful in overseeding of dormant warm season grasses since its lack of heat tolerance allows for a smooth transition for the warm-season grass. The ryegrass will provide a green cover during the winter months but will die out when the temperatures increases to the point which allow the warm-season grass to grow. The tetraploid perennial ryegrass of the present invention is different from all other known tetraploid perennial ryegrasses in that it has a leaf blade width of less that 6.50 mm, a leaf blade length of less than 37 cm, a leaf blade height of less than 35 cm, a leaf blade sheath length of less than 12 cm, a mature plant height of less than 72 cm, a spike length of less than 45 cm, a flag leaf sheath length of less than 17 cm, a flag leaf width of less than 6 mm, a flag leaf length of less than 30 cm, a flag leaf height of less than 47 cm, a lemma length of less than 8 mm, a lemma width of less than 2 mm, a glume length of less than 11 mm, a spike length of less than 235 mm, a spikelet length of less than 15 mm, and a 1,000 seed weight of less than 3,500 g.

DETAILED DESCRIPTION OF A PREFERRED EMBODIMENT

As used in the broad context in grasses, the term "overseeding" relates to the process of placing grass seed over an existing stand of turfgrass.

As used in the context of this document, the term "overseeding" relates only to the use of cool-season grasses sown into an existing warm season grass turf, for the purpose of having a green cover during the winter months when the warm-season grass is dormant.

| Species Used | Establishment | Color | Transition |
|---|---|---|---|
| Annual ryegrass | E | P | E |
| Tetraploid Perennial Ryegrass | E | E | E |
| Diploid Perennial ryegrass | VG | E | P-F |
| Poa trivialis | F | P | F |
| Intermediate ryegrass | VG | F-G | G |
| Meadow fescue | VG | G | E |

E = excellent
VG = very good
G = good
F = fair
P = poor

Key Elements in Overseeding Turfgrass.

Establishment—It is important in an overseeding grass to have rapid establishment. This includes a quick germination of the seed and the ability to tiller into areas adjacent to the next seedling.

Color—Many users of overseeding grasses prefer a dark green color. A light color grass can be made darker by applying iron. However, the user generally prefers to not do this unless the grass is too light in color.

Transition—A desirable transition grass is one that will die completely when the warm season grass is starting to reach its peak performance. The overseeding grass cannot die too quickly in the spring before the warm-season grass has an opportunity to grow.

Discussion of Current Species Used.

Annual ryegrass—Annual ryegrass was used extensively for overseeding prior to 1970. With breeding improvements of perennial ryegrass the use of annual ryegrass has declined. Annual ryegrass has an excellent germination rate but lacks tillering ability. Annual ryegrass is light in color and usually transitions too abruptly. The course leaf texture and very fast growth rate are undesirable.

Diploid Perennial ryegrass—Perennial ryegrass has a quick germination. It germinates slower than annual ryegrass but still within an acceptable range for the user. It has a very good tillering ability but in some cases it is too aggressive resulting in damage to the warm season grass. Newer cultivars of perennial ryegrass have excellent, dark green, color. The newer varieties of perennial ryegrass which are being sold as overseeding grasses were developed for permanent turf use. The result is a poor transitioning ability. This has resulted in the use of chemical applications to remove the perennial ryegrass. When this is necessary the turf has damage for several weeks, until the warm-season grass can recover.

Intermediate ryegrass—Intermediate ryegrass performance is more difficult to predict. It is a cross between annual and perennial ryegrass. If only one cross is made the performance is most similar to annual ryegrass. Each successive backcross to perennial ryegrass results in performance similar to diploid perennial ryegrass. A problem with current intermediate ryegrass is that it often transitions too rapidly, before the warm-season grass has a desirable level of performance.

Poa trivialis and Fine fescues—Both of these have slow germination and establishment. Because of this they are commonly used in mixtures with other grasses. The cost of producing these grasses is higher and as a result they are not usually used alone. The fine fescues have good transitioning ability compared to Poa trivialis.

Tetraploid Perennial Ryegrass—T3 has a rich very dark green color, high tiller density and slow vertical growth rate. Most tetraploid ryegrasses have been developed for forage use and therefore have a light color, poor turf density, and a rapid vertical growth rate. Tetraploid perennial ryegrass has a rapid germination rate and establishment rate and transitions when used in overseeding with Bermuda grass (warm-season). Tetraploid ryegrass transitions better than diploid perennial ryegrass.

Morphological Descriptors for Tetraploid Perennial Ryegrass

Genetic Color—the measure of the amount of lightness or darkness of green color. Recorded as a 1-9 subjective rating where 9=dark.

Growth Habit—the degree of erectness of a single plant. 1=prostrate (flat), 2=semi-prostrate, 3=horizontal, 7=semi-erect, 9=erect Inflorescence—the flowering portion of a grass plant.

Spike—in ryegrass the inflorescence is a primary spicate raceme.

Spike Length—measured from the upper most node to the apex of the inflorescence.

Node—the joint on a grass culm. A swollen region on the stem.

Leaf Blade—the flattened portion of a grass leaf located above the leaf sheath.

Leaf Blade Length—the length of the leaf blade. Measured on the first leaf subtending the flag leaf in cm.

Leaf Blade Width—measure of the width of the first blade subtending the flag leaf in mm taken 1 cm from the collar.

Leaf Blade Height—the height of the leaf blade from the ground to the collar in cm.

Leaf Sheath Length—the length of the leaf sheath. Measured on the first leaf subtending the flag leaf in cm.

Flag Leaf—the first leaf blade subtending the inflorescence.

Flag Leaf Length—the total length of a flag leaf which includes the sheath and blade. Measured from the uppermost node to the end of the upper most blade in cm.

Flag Leaf Width—the measure of the width of the flag leaf blade taken 1 cm from the collar of the flag leaf in mm.

Flag Leaf Height—the height of the flag leaf. Measured from the ground to the collar of the flag leaf in cm.

Flag Leaf Sheath Length—the sheath length of the flag leaf. Measured from the node to the collar in cm.

Mature Plant Height—the height in cm of a mature plant from the ground to the

Glume—the first pair of bracts at the base of a spikelet.

Spikelet—the basic unit of a grass inflorescence, includes glumes, lemmas, paleas and reproductive organs.

Floret—the portion of the spikelet that may include lemma, palea and reproductive organs.

Lemma—an odd nerved bract above the glumes.

Palea—the two nerved bract above the glumes.

Seed Size—the relative size of seeds usually measured by determining the number of seeds per pound.

1000-seed weight—the weight of 1,000 whole seeds.

Turfgrass Density—the number of tillers per unit area of a turfgrass sward.

Turf—a covering of mowed vegetation usually a grass.

Turfgrass—a species or cultivar of grass that is a mowed turf.

Turf Color—a visual and digital analysis score of the turfgrass community. When visual the color is measured on a scale of 1-9 with 9 being dark.

Turf Quality—the degree to which a turf conforms to a standard of uniformity, density, texture, growth habit, color and is generally taken as subjective data on a 1-9 scale with 9 being the best quality.

EXAMPLES

The following examples are furnished to further illustrate the present invention and are not intended to limit the invention beyond the examples set forth in the appended claim.

Example 1

Development of T3

In 1998, the breeding research program that resulted in the tetraploid perennial ryegrass variety T3 was initiated. The following breeding history describes the procedures used:

In August, 1998 sixty-three experimental lines were sent to Advanta B. V., Vlijmen, the Netherlands. The experimental lines originated from Advanta Seeds Pacific germplasm. The experimental lines were established in a single spaced plant nursery. The nursery consisted of 300 plants per line. The nursery was evaluated for; heading date, crown density, leaf texture, dark genetic color, and freedom from turf diseases (Fusarium sp.)

In the spring of 1999, fourteen top performing lines were removed from the nursery. The plants were moved to isolation and harvested by line. The seed was taken to the laboratory for chromosome doubling (Table 1).

TABLE 1

| Time Line | Chromosome Doubling Process |
| --- | --- |
| 1999 Day 1 | 1.5 grams of seed from each experimental line is weighed and replicated eight times. |
| | A check for each line is also weighed. |
| | The seeds are disinfected for 30 minutes in a 2% thiram solution. |
| | The seeds are then washed for two hours in a running water bath at 35 degree Celsius. |
| | The seeds are placed on blotting paper and dried for three hours at 35 degree Celsius. |
| | The seeds are then wrapped in a wet blotting paper for germination. The seeds are placed in a controlled environment; 21 degree Celsius for 24 hours. |
| 1999 Day 3 | The seeds are inspected for root length. The root length for optimal colchicine treatment is 2-3 mm. All the seeds with root length of 2-3 mm are placed in a petri dish. The seeds are kept separate by experimental line, as are the checks. |
| | Colchicine solution: 0.2 grams colchicine, 1 ml Tween 80, 1 ml DMSO, 98 ml distilled water. |

TABLE 1-continued

| Time Line | Chromosome Doubling Process |
|---|---|
| | Add 3 ml colchicine solution to each Petri dish; 3 ml of distilled water to the checks. Shake the Petri dishes gently for good distribution of the colchicine. Place the colchicine treated seeds in the dark for 2 hours at 30 degree Celsius. The seeds are placed in a strainer and rinsed with water for 15 minutes. The seeds are placed on blotting paper and placed in a germinator; 20 degree Celsius for 5-10 days. |
| 1999 Day 8-12 | The 4N plants can be removed from the other seedlings. The 4N plants are thicker. For many of the seeds, the colchicines will be lethal. For some of the seeds the colchicine will not enter the tissue, resulting in normal 2N plants. The 4N plants are planted in soil and moved to the greenhouse. |
| 2000 Spring | Pollen is collected from the plants to determine that the plants are 4N. Those plants which are 4N are moved to the field. At this point all 14 experimental lines are merged into one population. |
| 2000 Fall | Before harvest the plants are analyzed again for only 4N plants. This insures purity. Ploidy level is determined using a flowcytometer. |

In the spring of 2000, one-hundred-thirteen plants were moved to the field from the colchocine treatment. The 113 plants were combined from the 14 different experimental lines. In July the 113 plants were harvested. In the fall, a nursery was established to again confirm that all plants were 4N. The nursery consisted of 500 plants. The confirmation was done in the spring of 2001. All 113 plants were confirmed to be 4N. The 500 plants were harvested in July 2001.

In May 2003, the seed was sent to Advanta Seeds Pacific for further evaluation. In September, a single spaced plant nursery was established. The nursery contained 500 plants; 100 plants per replication.

May 2004, the nursery was evaluated for; dark genetic color, fine leaf texture, crown density, and freedom from disease (*Puccinia graminis*). One hundred-nine plants were selected. The 109 plants were confirmed to be 4N, with a flowcytometer. The 109 plants were moved before flowering to an isolated crossing block. The block was harvested by progeny. Only those plants which produced over 40 grams per plant were bulked to make the cultivar T3, tetraploid perennial ryegrass.

Example 2

T3 is the first tetraploid perennial ryegrass used for turf application. T3 is also the first tetraploid perennial ryegrass that exhibits a fine leaf texture and dark leaf color, which is more similar to diploid perennial ryegrass. Leaf color is the density of chlorophyll in the leaf blade, resulting in the intensity of color. In the turfgrass industry, dark green color is preferred. The dark green color gives an impression of a more healthy vigorous turf.

Turf color can be measured quantitatively and qualitatively. a) In Table 2, the relative color of the different cultivars were scored using a 1-9 visual scale, 9 being the darkest green. Table 2 shows the comparisons between diploid and tetraploid perennial ryegrass. b) Digital analysis can also be used to determine color. A digital picture is taken of the turf. The software program Sigma Scan is used to convert the pixel image to a standard color wheel (hue, saturation and brightness). It then generates a number on a 1-9 scale, with 9 being the darkest green.

Both visual and digital camera comparisons (Table 2) show that T3 is equal to current turf type diploid perennial ryegrass. The turf color of T3 is most similar to Applaud.

Table 2, illustrates the visual comparisons for several cultivars taken in Albany, Oregon during 2004-2005. The ratings are based on the following: 1=light green; 3=medium-light green; 5=medium green; 7=medium-dark green; 9=dark green.

TABLE 2

Genetic Color Ratings
(Albany, Oregon - 2004/2005)

| Type/Usage | Cultivar | Visual Rating | Digital Rating |
|---|---|---|---|
| Tetraploid Turf | T3 | 7.17 | 7.02 |
| Diploid Turf | Applaud | 6.76 | 7.20 |
| Diploid Turf | Yorktown III | 4.59 | 4.86 |
| Diploid Turf | Palmer III | 5.88 | 6.32 |
| Tetraploid Forage | Bastion C1 | 4.92 | 3.52 |
| | LSD (0.05) | 0.57 | 0.27 |

Example 3

T3 is the first tetraploid perennial ryegrass with finer leaf blade characteristics. The measurements that best describe the leaf blade are: a) width; b) length; c) height; d) sheath length. One of the desirable qualities of a cool season turf is the relative fineness of the leaf blade. A wider—longer leaf blade results in a more course appearance, which is undesirable. T3 has leaf blade characteristics significantly less than the tetraploid forage grasses, but slightly larger than diploid perennial turf types. Leaf blade measurements are given in Table 3.

TABLE 3

Leaf Blade Measurements
(Albany, Oregon - 2004/2005)

| Type/Usage | Cultivar | Leaf Blade Width (mm) | Leaf Blade Length (cm) | Leaf Blade Height (cm) | Leaf Blade Sheath Length (cm) |
|---|---|---|---|---|---|
| Tetraploid Turf | T3 | 5.33 | 27.9 | 26.53 | 9.30 |
| Diploid Turf | Amazing | 4.27 | 21.1 | 20.20 | 6.93 |
| Diploid Turf | Brightstar | 3.70 | 20.3 | 17.47 | 6.83 |
| Tetraploid Forage | Aubisque | 6.27 | 35.87 | 34.67 | 10.97 |
| Tetraploid Forage | Bastion | 6.4 | 36.4 | 28.73 | 11.4 |
| | LSD (0.05) | 0.50 | 2.24 | 2.09 | 0.85 |

Example 4

T3 is the first turf type tetraploid perennial ryegrass with a reduced plant height. Forage grasses, especially tetraploids, produce a taller, more stalwart plant. In turf, a lower growth habit is more desirable because: a) a faster vertical growth rate results in increased mowing, and b) more biomass is produced. For turf applications a faster growth rate and increased biomass are not favorable.

Table 4 shows that T3 is the first turf-type tetraploid perennial ryegrass with a reduced plant height compared to tetraploid forage grasses;

TABLE 4

Mature Plant Height
(Albany, Oregon - 2004)

| Type/Usage | Cultivar | Mature Plant Height (cm) |
|---|---|---|
| Tetraploid Turf | T3 | 70.40 |
| Diploid Turf | Amazing | 57.43 |
| Diploid Turf | Brightstar | 56.93 |
| Tetraploid Forage | Aubisque | 88.33 |
| Tetraploid Forage | Bastion | 89.93 |
| | LSD (0.05) | 5.17 |

Example 5

T3 is the first turf-type tetraploid perennial ryegrass that has a shorter spike length. A growth rate more similar to turf-type diploid perennial ryegrass is preferred because the mowing frequency is reduced which reduces the stress on the plant. This reduced stress improves the quality of the turf. All forage tetraploid perennial ryegrass have been selected for increased growth.

Table 5 shows that T3 has a reduced spike length, more similar to turf-type diploid perennial ryegrass.

TABLE 5

Spike Length
(Albany, Oregon - 2004/2005)

| Type/Usage | Cultivar | Spike Length (cm) |
|---|---|---|
| Tetraploid Turf | T3 | 42.33 |
| Diploid Turf | Amazing | 33.00 |
| Diploid Turf | Brightstar | 35.77 |
| Tetraploid Forage | Aubisque | 50.80 |
| Tetraploid Forage | Bastion | 55.93 |
| | LSD (0.05) | 2.54 |

Example 6

T3 is the first tetraploid perennial ryegrass that the flag leaf characteristics are reduced compared to the tetraploid forages. Tetraploid forage grasses have been selected for increased plant size. Diploid turf grasses have been selected for decreased plant size. The flag leaf characteristics: a) length; b) width; c) height; d) sheath length are an indicator of overall plant size.

Table 6 shows that the flag leaf characteristics; length, width, height, and sheath length of T3 are shorter than tetraploid forage, but more intermediate to turf-type diploid perennial ryegrass.

TABLE 6

Flag Leaf Measurements
(Albany, Oregon - 2004/2005)

| Type/Usage | Cultivar | Flag Leaf Length (cm) | Flag Leaf Width (mm) | Flag Leaf Height (cm) | Flag Leaf Sheath Length (cm) |
|---|---|---|---|---|---|
| Tetraploid Turf | T3 | 29.73 | 5.10 | 44.00 | 14.13 |
| Diploid Turf | Amazing | 22.07 | 3.73 | 33.43 | 10.47 |
| Diploid Turf | Brightstar | 21.17 | 3.33 | 30.67 | 10.67 |
| Tetraploid Forage | Aubisque | 37.93 | 6.13 | 56.63 | 17.00 |

TABLE 6-continued

Flag Leaf Measurements
(Albany, Oregon - 2004/2005)

| Type/Usage | Cultivar | Flag Leaf Length (cm) | Flag Leaf Width (mm) | Flag Leaf Height (cm) | Flag Leaf Sheath Length (cm) |
|---|---|---|---|---|---|
| Tetraploid Forage | Bastion | 38.70 | 6.07 | 50.47 | 16.10 |
| | LSD (0.05) | 1.49 | 0.52 | 3.05 | 0.83 |

Example 7

T3 is the first tetraploid turf-type perennial ryegrass with a smaller seed size compared to tetraploid forage, but approaching turf-type diploid perennial ryegrass. Seed size is an important trait in the turfgrass industry for two reasons: a) a seed of smaller size allows for ease of distribution over the seed bed; b) a smaller seed relates to more seeds per pound. This results in more seeds being disbursed over the seeding area. This allows more seeds to germinate and establish in a given area. Seed size can be determined with several measurements: a) lemma length; b) lemma width; c) glume length; d) 1,000 seed weight.

Table 7 shows the 1,000 seed weights (in grams) of T3 in comparison to diploid turf and tertraploid forage perennial ryegrass.

TABLE 7

1,000 Seed Weight
(Albany, Oregon - 2004/2005)

| Type/Usage | Cultivar | 1,000 Seed Weight (grams) |
|---|---|---|
| Tetraploid Turf | T3 | 2409 |
| Diploid Turf | Amazing | 1754 |
| Diploid Turf | Brightstar | 1967 |
| Tetraploid Forage | Aubisque | 2942 |
| Tetraploid Forage | Bastion | 2903 |

Table 8 shows the lemma length (mm) of T3 in comparison to diploid turf and tetraploid forage perennial ryegrass.

TABLE 8

Lemma Length
(Albany, Oregon - 2004/2005)

| Type/Usage | Cultivar | Lemma Length (mm) |
|---|---|---|
| Tetraploid Turf | T3 | 7.33 |
| Diploid Turf | Amazing | 5.53 |
| Diploid Turf | Brightstar | 5.80 |
| Tetraploid Forage | Aubisque | 8.03 |
| Tetraploid Forage | Bastion | 8.07 |
| | LSD (0.05) | 0.13 |

Table 9 shows the lemma width (mm) of T3 in comparison to diploid turf and tetraploid forage perennial ryegrass.

TABLE 9

Lemma Width
(Albany, Oregon - 2004/2005)

| Type/Usage | Cultivar | Lemma Width (mm) |
|---|---|---|
| Tetraploid Turf | T3 | 1.53 |
| Diploid Turf | Amazing | 1.20 |

TABLE 9-continued

Lemma Width
(Albany, Oregon - 2004/2005)

| Type/Usage | Cultivar | Lemma Width (mm) |
|---|---|---|
| Diploid Turf | Brightstar | 1.23 |
| Tetraploid Forage | Aubisque | 1.6 |
| Tetraploid Forage | Bastion | 1.6 |
| | LSD (0.05) | 0.006 |

Table 10 shows the glume length (mm) of T3 in comparison to diploid turf and tetraploid forage perennial ryegrass.

TABLE 10

Glume Length
(Albany, Oregon - 2004/2005)

| Type/Usage | Cultivar | Glume Length (mm) |
|---|---|---|
| Tetraploid Turf | T3 | 10.03 |
| Diploid Turf | Amazing | 7.13 |
| Diploid Turf | Brightstar | 7.40 |
| Tetraploid Forage | Aubisque | 12.03 |
| Tetraploid Forage | Bastion | 11.97 |
| | LSD (0.05) | 0.50 |

Example 8

T3 is the first tetraploid turf-type perennial ryegrass to produce spike characteristics more similar to diploid turf-type perennial ryegrass. Spike characteristics are important to the number of seeds produced per plant, resulting in the overall yield of the cultivar. Cultivars which produce low seed yields are not desirable. Tetraploid forage perennial ryegrass is characterized by the inability to produce many seeds per spike. The panicle traits: a) length of spike; b) spikelets per spike; c) length of spikelet; d) spike weight contribute to the yield potential of a cultivar. Tables 11-14 illustrate that T3 is intermediate between diploid turf-type perennial ryegrass and tetraploid forage ryegrass.

TABLE 11

Length of Spike
(Albany, Oregon - 2004/2005)

| Type/Usage | Cultivar | Spike Length (mm) |
|---|---|---|
| Tetraploid Turf | T3 | 233.27 |
| Diploid Turf | Amazing | 158.53 |
| Diploid Turf | Brightstar | 175.60 |
| Tetraploid Forage | Aubisque | 270.43 |
| Tetraploid Forage | Bastion | 266.90 |
| | LSD (0.05) | 10.07 |

Table 12 shows the spikelet length of T3 in comparison to diploid and teraploid perennial ryegrasses.

TABLE 12

Spikelet Length
(Albany, Oregon - 2004/2005)

| Type/Usage | Cultivar | Spikelet Length (mm) |
|---|---|---|
| Tetraploid Turf | T3 | 14.90 |
| Diploid Turf | Amazing | 11.60 |
| Diploid Turf | Brightstar | 12.17 |
| Tetraploid Forage | Aubisque | 16.80 |
| Tetraploid Forage | Bastion | 17.00 |
| | LSD (0.05) | 0.73 |

Table 13 shows spike weight (grams) of T3 in comparison to diploid turf and tetraploid perennial ryegrass.

TABLE 13

Spike Weight
(Albany, Oregon - 2004/2005)

| Type/Usage | Cultivar | Spike Weight (grams) |
|---|---|---|
| Tetraploid Turf | T3 | 0.453 |
| Diploid Turf | Amazing | 0.260 |
| Diploid Turf | Brightstar | 0.261 |
| Tetraploid Forage | Aubisque | 0.597 |
| Tetraploid Forage | Bastion | 0.569 |
| | LSD (0.05) | 0.039 |

Example 9

T3 is the first tetraploid perennial ryegrass with desirable overseeding characteristics. Turfgrass managers require a grass that can establish quickly and then transition rapidly. Turfgrass managers also require high turf quality, a dark green color, slow vertical growth rate, and the ability to mow without shredding. Tables 14-18 shows T3 in comparison to other grasses used in overseeded Bermudagrass.

Tables 14-18 are a summary of data collected from University overseeding trials. The trials were conducted at the University of Arkansas, Fayetteville, Ark. and Auburn University, Auburn, Ala. The trial was designed as a dual test. The entries, management, and ratings were the same at each site.

Table 14 shows the establishment rate in comparison to other grasses used in overseeded Bermudagrass turf. The data is presented on a 0-9 scale; with 9 being 100% established.

TABLE 14

Establishment Rate
(Fayetteville, Arkansas - 2004/2005)
(Auburn, Alabama - 2004/2005)

| Entry | Establishment Day 6 | | Establishment Day 12 | | Establishment Day 14 | |
|---|---|---|---|---|---|---|
| | Arkansas | Alabama | Arkansas | Alabama | Arkansas | Alabama |
| Intermediate Ryegrass | 5.00 | 4.30 | 9.00 | 6.30 | 9.00 | 9.00 |
| Diploid Perennial Ryegrass | 3.30 | 4.80 | 7.30 | 6.80 | 9.00 | 8.80 |

TABLE 14-continued

Establishment Rate
(Fayetteville, Arkansas - 2004/2005)
(Auburn, Alabama - 2004/2005)

| Entry | Establishment Day 6 | | Establishment Day 12 | | Establishment Day 14 | |
|---|---|---|---|---|---|---|
| | Arkansas | Alabama | Arkansas | Alabama | Arkansas | Alabama |
| *Poa trivialis* | 1.00 | 1.00 | 2.30 | 2.00 | 4.30 | 6.80 |
| Meadow Fescue | 2.30 | 4.30 | 5.50 | 6.30 | 7.50 | 8.80 |
| 'T3' Tetraploid Perennial Ryegrass | 2.00 | 4.50 | 7.30 | 6.30 | 9.00 | 9.00 |
| Non-Overseeded Bermudagrass Check | 0.00 | 0.00 | 0.00 | 0.00 | 0.00 | 0.00 |
| LSD (P = .05) | 1.42 | 0.76 | 1.48 | 1.13 | 0.59 | 0.55 |

Table 15 shows the turf quality and turf color in comparison to other grasses used in overseeded Bermudagrass turf. In Table 15, the relative color and density of the different cultivars was scored using a 1-9 scale; with 9 being the darkest green or most dense.

TABLE 15

Turf Quality and Turf Color
(Fayetteville, Arkansas - 2004/2005)
(Auburn, Alabama - 2004/2005)

| | Turf Quality 2004-2005 Average | | Turf Color 2004-2005 Average | |
|---|---|---|---|---|
| Entry | Arkansas | Alabama | Arkansas | Alabama |
| Intermediate Ryegrass | 5.80 | 6.60 | 5.50 | 6.40 |
| Diploid Perennial Ryegrass | 6.70 | 6.70 | 7.40 | 6.90 |
| *Poa trivialis* | 3.40 | 6.00 | 5.10 | 5.90 |
| Meadow Fescue | 5.40 | 6.20 | 5.30 | 6.20 |
| 'T3' Tetraploid Perennial Ryegrass | 5.70 | 6.70 | 7.20 | 7.10 |
| Non-Overseeded Bermudagrass Check | 2.10 | 3.30 | 2.30 | 3.30 |
| LSD (P = .05) | 0.70 | 0.20 | 0.60 | 0.20 |

Table 16 presents the mowing quality displayed by T3 in comparison to other grasses used in overseeded Bermudagrass turf. In Table 16, the relative mowing qualities of the different cultivars was scored using a 1-9 scale; with 9 being best.

TABLE 16

Mowing Quality
(Fayetteville, Arkansas - 2004/2005)
(Auburn, Alabama - 2004/2005)

| Entry | Mowing Quality Arkansas |
|---|---|
| Intermediate Ryegrass | 5.90 |
| Diploid Perennial Ryegrass | 6.30 |
| *Poa trivialis* | 6.10 |

TABLE 16-continued

Mowing Quality
(Fayetteville, Arkansas - 2004/2005)
(Auburn, Alabama - 2004/2005)

| Entry | Mowing Quality Arkansas |
|---|---|
| Meadow Fescue | 6.70 |
| 'T3' Tetraploid Perennial Ryegrass | 6.00 |
| Non-Overseeded Bermudagrass Check | 2.10 |
| LSD (P = .05) | 0.40 |

Table 17 helps to illustrate vertical extension. The higher the clipping yield the greater the vertical extension (growth rate) which results in frequent mowing, a non-desirable trait. The clipping yields are reported in grams per plot (Alabama data), and grams/meter$^2$ (Arkansas).

TABLE 17

Clipping Yield
(Fayetteville, Arkansas - 2004/2005)
(Auburn, Alabama - 2004/2005)

| | Clipping Yield May | |
|---|---|---|
| Entry | Arkansas | Alabama |
| Intermediate Ryegrass | 19.00 | 81.80 |
| Diploid Perennial Ryegrass | 16.20 | 65.30 |
| *Poa trivialis* | 15.70 | 67.00 |
| Meadow Fescue | 21.80 | 63.10 |
| 'T3' Tetraploid Perennial Ryegrass | 17.50 | 49.90 |
| Non-Overseeded Bermudagrass Check | 10.20 | 20.70 |
| LSD (P = .05) | 2.50 | 21.50 |

Table 18 shows the percent of Bermudagrass present of T3 in comparison to other grasses used in overseeded Bermudagrass turf. The higher percentage relates to a more complete transition.

TABLE 18

Transition Data - % Bermuda grass
(Fayetteville, Arkansas - 2004/2005)
(Auburn, Alabama - 2004/2005)

| Entry | % Bermudagrass Present May | | % Bermudagrass Present June | | % Bermudagrass Present July | |
|---|---|---|---|---|---|---|
| | Arkansas | Alabama | Arkansas | Alabama | Arkansas | Alabama |
| Intermediate Ryegrass | 23.80 | 48.80 | 72.50 | 74.50 | 88.80 | 87.80 |
| Diploid Perennial Ryegrass | 10.00 | 48.80 | 45.00 | 74.50 | 81.30 | 84.50 |
| Poa trivialis | 37.50 | 40.00 | 65.00 | 53.80 | 83.30 | 67.00 |
| Meadow Fescue | 20.00 | 52.50 | 75.00 | 73.80 | 92.50 | 83.80 |
| 'T3' Tetraploid Perennial Ryegrass | 17.50 | 48.80 | 77.50 | 75.00 | 97.00 | 87.00 |
| Non-Overseeded Bermudagrass Check | 90.00 | 91.30 | 100.00 | 100.00 | 100.00 | 100.00 |
| LSD (P = .05) | 7.20 | 6.60 | 13.10 | 5.20 | 9.40 | 6.90 |

Deposit Statement

Applicant has made a deposit of at least 2500 seeds of tetraploid perennial ryegrass T3 with the American Type Culture Collection (ATCC), Manassas, Va., under deposit accession number PTA-6495. The seeds deposited with the ATCC were taken from the deposit maintained by Advanta Seeds Pacific, Inc., 33725 Columbus Street, S.E., Albany. Oreg. 93722-7246 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. Section 1.808. This deposit of the tetraploid ryegrass variety T3 will be maintained in the ATCC deposito, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. Sections 1.801-1.809, including providing an indication of the viability of the sample upon deposit. Applicant has no authority to waive any restrictions imposed by law on the transfer of biological material or its transportation in commerce.

The preceding invention has been described in some detail by way of example for purposes of clarity and understanding, it will be obvious that certain changes and modifications may be practiced within the scope of the invention, as limited only by the scope of the appended claims.

I claim:

1. A tetraploid perennial ryegrass variety T3, a representative sample of seed of said variety deposited under American Type Culture Collection accession number PTA-6495.
2. A seed of the variety of claim 1.
3. A ryegrass plant, or a part thereof, produced by growing seed of claim 2.
4. Pollen of the plant of claim 3.
5. An ovule of the plant of claim 3.
6. A ryegrass plant, or a part thereof, having all the physiological and morphological characteristics of the tetraploid ryegrass plant of claim 3.
7. A ryegrass produced by growing seed from the ryegrass plant of claim 3.
8. A ryegrass produced vegetatively from the ryegrass plant, or a part thereof, of claim 3.
9. A method for producing turfgrass seed, comprising the steps of crossing the turfgrass plant of claim 3 with a different turfgrass plant and harvesting seed produced.

* * * * *